United States Patent
Arnin

(10) Patent No.: US 9,427,331 B2
(45) Date of Patent: Aug. 30, 2016

(54) SPINAL CAGE

(71) Applicant: Uri Arnin, Kiryat Tivon (IL)

(72) Inventor: Uri Arnin, Kiryat Tivon (IL)

(73) Assignee: Apifix Ltd., Carmiel (IL)

( * ) Notice: Subject to any disclaimer, the term of this patent is extended or adjusted under 35 U.S.C. 154(b) by 0 days.

(21) Appl. No.: 14/331,351

(22) Filed: Jul. 15, 2014

(65) Prior Publication Data

US 2016/0015522 A1 Jan. 21, 2016

(51) Int. Cl.
*A61F 2/44* (2006.01)
*A61F 2/30* (2006.01)

(52) U.S. Cl.
CPC .............. *A61F 2/447* (2013.01); *A61F 2/4425* (2013.01); *A61F 2002/30471* (2013.01); *A61F 2002/30538* (2013.01); *A61F 2002/30556* (2013.01); *A61F 2002/30579* (2013.01)

(58) Field of Classification Search
CPC ................. A61F 2/4425; A61F 2002/443
See application file for complete search history.

(56) References Cited

U.S. PATENT DOCUMENTS

| | | | |
|---|---|---|---|
| 6,176,882 B1* | 1/2001 | Biedermann | A61F 2/447 623/17.11 |
| 6,685,742 B1* | 2/2004 | Jackson | A61F 2/447 623/17.11 |
| 2004/0002761 A1* | 1/2004 | Rogers et al. | 623/17.13 |
| 2008/0071375 A1* | 3/2008 | Carver et al. | 623/17.13 |
| 2008/0082169 A1* | 4/2008 | Gittings et al. | 623/17.16 |
| 2013/0158664 A1* | 6/2013 | Palmatier et al. | 623/17.16 |

\* cited by examiner

*Primary Examiner* — Nicholas Plionis
(74) *Attorney, Agent, or Firm* — Dekel Patent Ltd.; David Klein

(57) ABSTRACT

A spinal cage includes first and second spinal attachment members attachable to vertebrae, the first and second spinal attachment members articulating with one another by means of an articulation joint, and a wedge element arranged for wedging between the first and second spinal attachment members. An actuator is linked to the wedge element for moving the wedge element axially with respect to the first and second spinal attachment members. The actuator includes a threaded member adjacent the wedge element and a biasing device positioned between at least one of the first and second spinal attachment members and the wedge element. Upon turning of the threaded member, the wedge element is advanced with respect to the articulation joint so that the first and second spinal attachment members are tilted or parallel to each other. The biasing device applies a biasing force on the wedge element to move the wedge element axially.

12 Claims, 3 Drawing Sheets

SPINAL CAGE

FIELD OF THE INVENTION

The present invention relates generally to spinal implants and prostheses, and particularly to a rotatable spinal cage.

BACKGROUND OF THE INVENTION

Scoliosis is a spinal deformity affecting many people. Current surgical treatment involves affixing long fusion rods to the spine by pedicle screws. The rod system is intended to force the deformed spine into a more healthy position. Other spinal disorders which are often treated by fusion include hyperkyphosis and hyperlordosis.

PCT Patent Application PCT/US2013/020454 describes a spinal cage that has a rotational pivot and a mechanism to allow rotation in one direction while preventing rotation in the opposite direction.

SUMMARY OF THE INVENTION

The present invention also seeks to provide an improved way to correct spinal deformity by using a spinal cage inserted between adjacent vertebral bodies. The spinal cage is built in a way that it has a rotational pivot and a mechanism to allow rotation in one direction while preventing rotation in the opposite direction. The spinal cage may be used, for example, to correct lordosis of the spine or other disorders.

In one embodiment of the present invention, the spinal cage includes first and second spinal attachment members attachable to vertebrae, the first and second spinal attachment members articulating with one another by means of an articulation joint, and a wedge element arranged for wedging between the first and second spinal attachment members. An actuator is linked to the wedge element for moving the wedge element axially with respect to the first and second spinal attachment members. The actuator includes a threaded member attached to the wedge element and a biasing device positioned between at least one of the first and second spinal attachment members and the wedge element. Upon turning of the threaded member, the wedge element is either advanced or retracted with respect to the articulation joint so that the first and second spinal attachment members are either tilted or parallel to each other. The biasing device applies a biasing force on the wedge element to move the wedge element axially.

BRIEF DESCRIPTION OF DRAWINGS

The present invention will be understood and appreciated more fully from the following detailed description, taken in conjunction with the drawings in which.

DETAILED DESCRIPTION OF EMBODIMENTS

Figure 1:
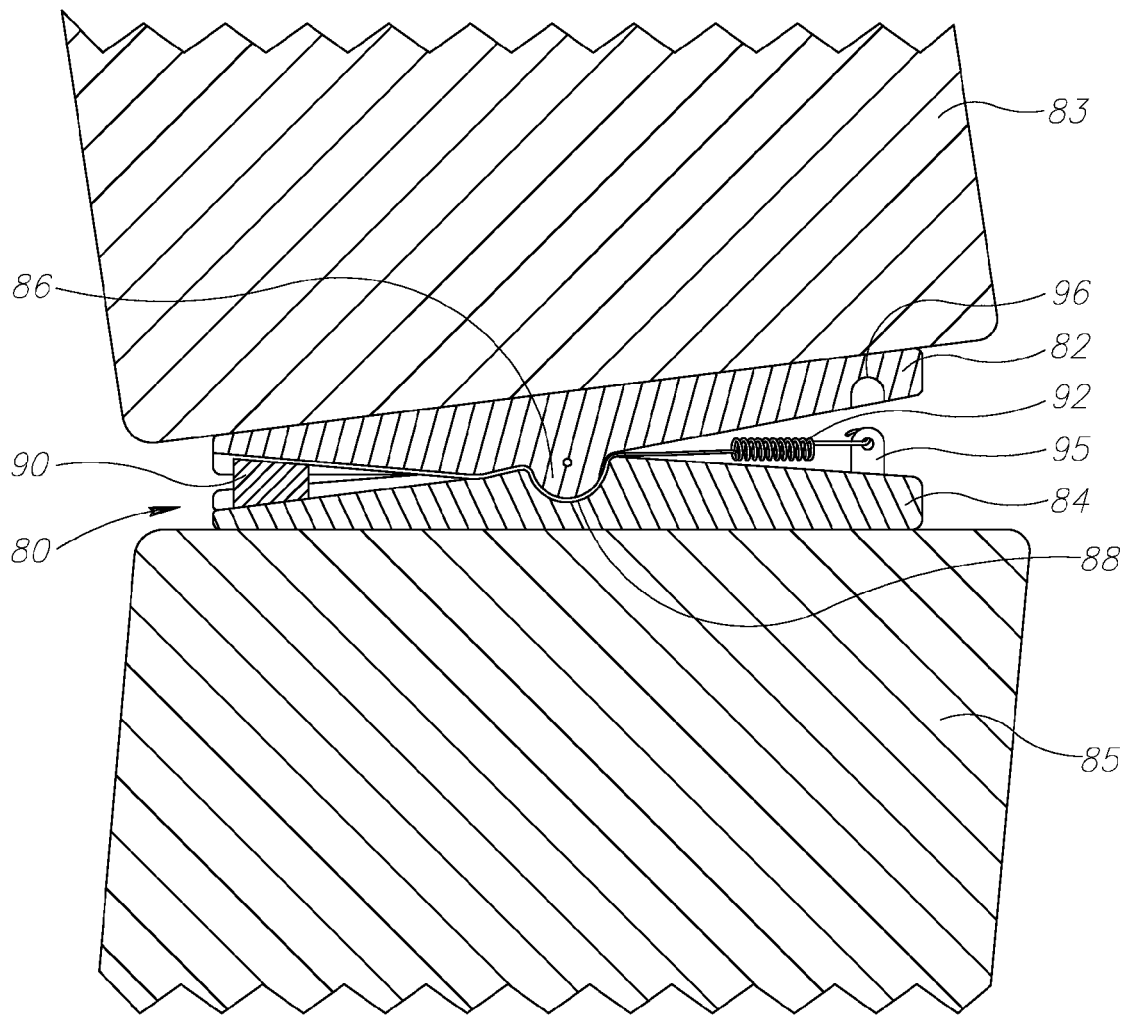
FIG. 1 is a simplified pictorial illustration of a longitudinal cross section of a uni-directional rotatable spinal cage of the prior art, PCT Patent Application PCT/US2013/020454.
Figure 2:
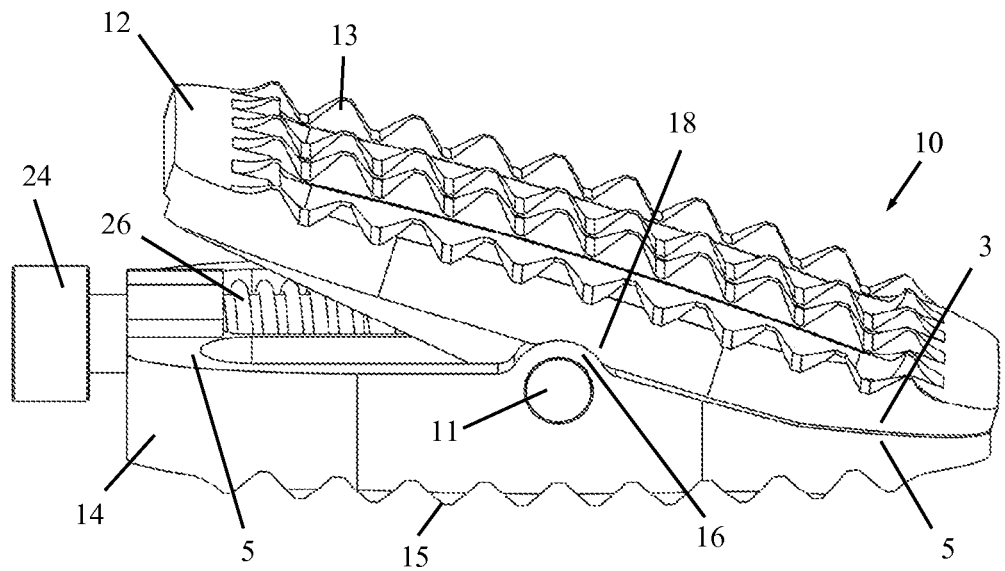
FIGS. 2 and 3 are simplified pictorial and top-view illustrations, respectively, of a spinal cage having first and second spinal attachment members, constructed and operative in accordance with a non-limiting embodiment of the present invention, with the first spinal attachment member in respective tilted and horizontal orientations.

Reference is now made to FIG. 1, which illustrates a rotatable spinal cage 80 of the prior art, PCT Patent Application PCT/US2013/020454.

Spinal cage 80 includes first and second spinal attachment members 82 and 84, such as flat plates. First and second spinal attachment members 82 and 84 are attached to two adjacent vertebrae 83 and 85, respectively. The plates may have coarse or roughened surfaces that interface with the vertebrae for enhanced binding to the vertebra bone or tissue (other adhesion enhancers may be used as well, such as coatings for binding with tissue and the like). For example, fixation of spinal cage 80 can be enhanced by means of spikes, screws or other means known to those skilled in the art.

First and second spinal attachment members 82 and 84 articulate with one another by means of an articulation joint. Accordingly, spinal cage 80 can pivot about the articulation joint in one rotational degree of freedom. In the illustrated embodiment, the articulation joint includes a male member 86 which is pivotally received in a female member 88. In the illustrated embodiment, the male member 86 extends from first spinal attachment member 82 and the female member 88 is formed in second spinal attachment member 84. The reverse can also be made.

A wedge element 90 is arranged for wedging between first and second spinal attachment members 82 and 84. Wedge element 90 may have a generally conical or trapezoidal shape or any other shape that can be accommodated by first and second spinal attachment members 82 and 84. An actuator 92 is linked to wedge element 90 for moving wedge element 90 in a direction that wedges wedge element 90 further in between members 82 and 84 (i.e., increases the wedging effect) or further away from members 82 and 84 (i.e., decreases the wedging effect). Actuator 92 can be, without limitation, a spring, motor, linear actuator, solenoid and the like. Actuator 92 can pull or push wedge element 90 directly or through a string, rod or any other connecting element.

The surfaces of first and second spinal attachment members 82 and 84 that contact wedge element 90 can be polished, roughened, grooved, etc., to increase the friction between the wedge and the members. In one embodiment, wedge element 90 can have a threaded hole, pin, groove and the like, for grasping with a tool to enable pulling the wedge and to release the uni-directional mechanism and allow some rotation of the attachment members 82 and 84 to another direction.

There are several features of the prior art wedge mechanism that should be noted.

First, the wedge element 90 and actuator 92 are positioned on opposite sides of the articulation joint.

Second, since the wedge element 90 is moved in the wedging direction only by the uni-directional mechanism (unless released and pulled by some grasping tool in a direction opposite to the wedging direction), it is desirable to increase the friction between the wedge element 90 and the spinal attachment members 82 and 84, so that wedge element 90 does not slip.

Reference is now made to FIGS. 2-5, which illustrate a spinal cage 10, constructed and operative in accordance with a non-limiting embodiment of the present invention.

Spinal cage 10 includes first and second spinal attachment members 12 and 14, each of which has bone-interface surfaces 13 and 15, respectively, attachable to vertebrae. The bone-interface surfaces 13 and 15 may be configured to promote osseointegration by increasing their surface area. For example, in the illustrated embodiment, bone-interface surfaces 13 and 15 are roughened, such as by means of a plurality of teeth. Additionally or alternatively, the surfaces 13 and 15 may be roughened in other manners, such as, by acid-etching, grit blasting, and/or machining. Additionally or alternatively, the surfaces 13 and 15 can be coated to promote osseointegration. Calcium phosphate ceramics, such as tricalcium phosphate (TCP) and hydroxyapatite (HA) are examples of materials that can enhance osseointegration of the surfaces 13 and 15. Additionally or alternatively, the surfaces 13 and 15 can comprise macroscopic structures, such as, for example, threads, micro-threads, indentations, and/or grooves that are configured to promote osseointegration and can be used alone or combined with the roughening and/or the coatings described above.

First and second spinal attachment members 12 and 14 have inner surfaces 3 and 5, respectively (opposite to bone-interface surfaces 13 and 15). Distal and/or proximal portions of inner surfaces 3 and 5 may be curved to provide increased tilting between first and second spinal attachment members 12 and 14. For example, the distal and/or proximal portion of inner surface 3 of first spinal attachment member 12 may be convex while the distal portion of inner surface 5 of second spinal attachment member 14 may be concave.

The bone-interface surfaces 13 and 15 of first and second spinal attachment members 12 and 14 may be flat. Alternatively, surfaces 13 and 15 may be curved or otherwise shaped to match the anatomical shape of the vertebra or other spinal structure to which they are designed to be attached. Additionally or alternatively, the geometrical shapes of first and second spinal attachment members 12 and 14 may be configured to accommodate the lordosis angle between adjacent vertebrae.

First and second spinal attachment members 12 and 14 articulate with one another by means of an articulation joint 11. In the illustrated embodiment, the articulation joint 11 includes a male member 16 which is pivotally received in a female member 18. In the illustrated embodiment, the male member 16 extends from second spinal attachment member 14 and the female member 18 is formed in first spinal attachment member 12. Of course, the reverse can also be made.

Figure 4:
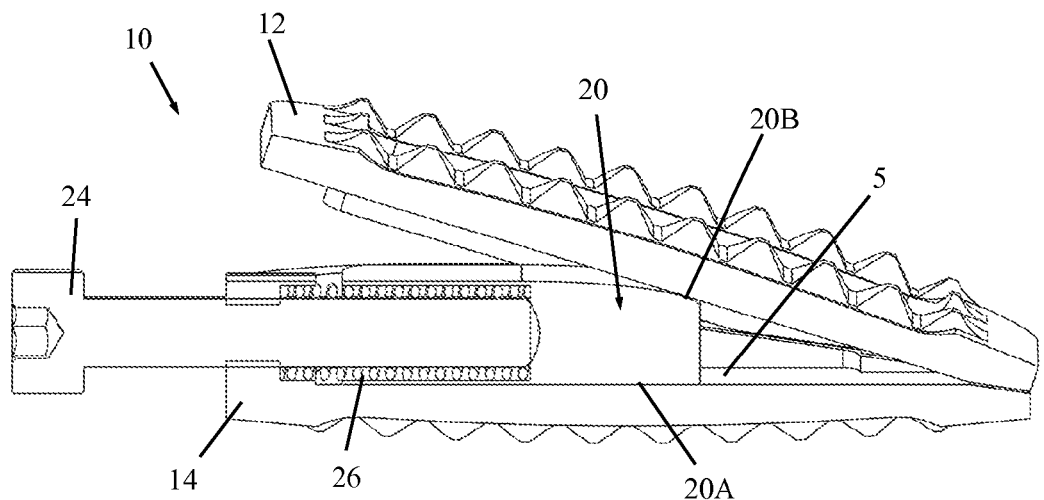
FIGS. 4 and 5 are simplified side-view illustrations of the spinal cage with the first spinal attachment member in respective tilted and horizontal orientations.

A wedge element 20 (FIG. 4) is arranged for wedging between first and second spinal attachment members 12 and 14. Wedge element 20 may have a generally conical or trapezoidal shape or any other shape that can be accommodated by first and second spinal attachment members 12 and 14. In the illustrated embodiment, wedge element 20 has a generally flat surface 20A that slides over the inner surface 5 of second spinal attachment member 14 and a chamfered surface 20B that wedges against the inner surface 3 of first spinal attachment member 12 (FIG. 4). Wedge element 20 may be shaped such that at any position it is geometrically locked with respect to first and second spinal attachment members 12 and 14.

Figure 3:
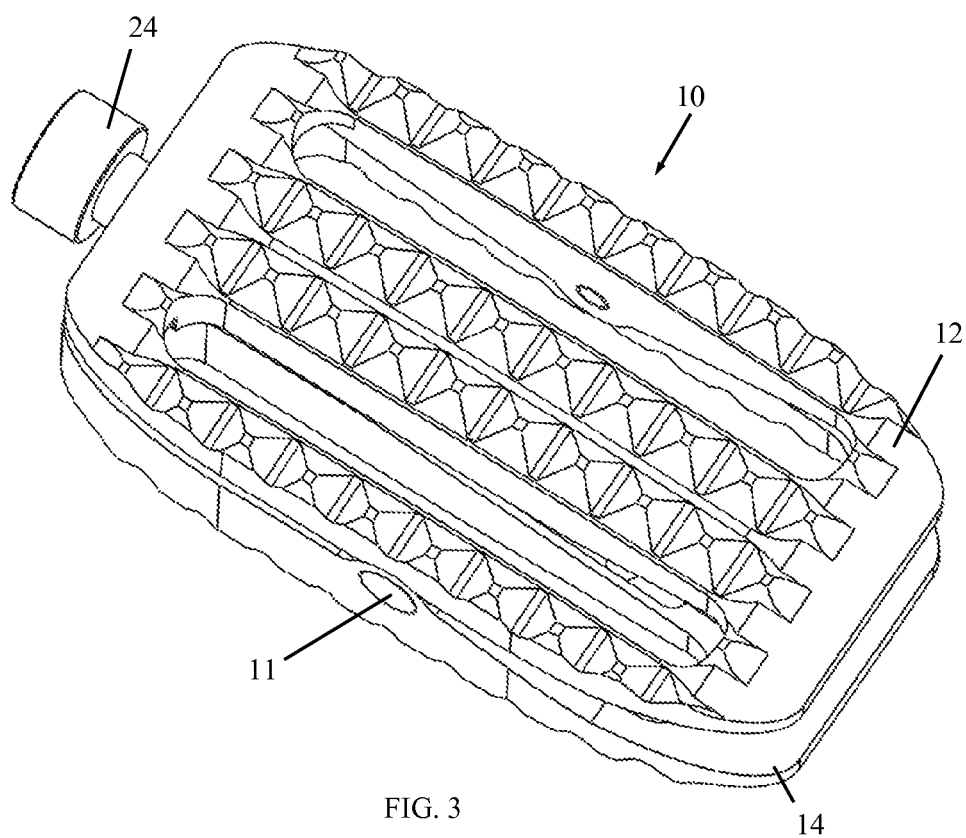
Figure 5:
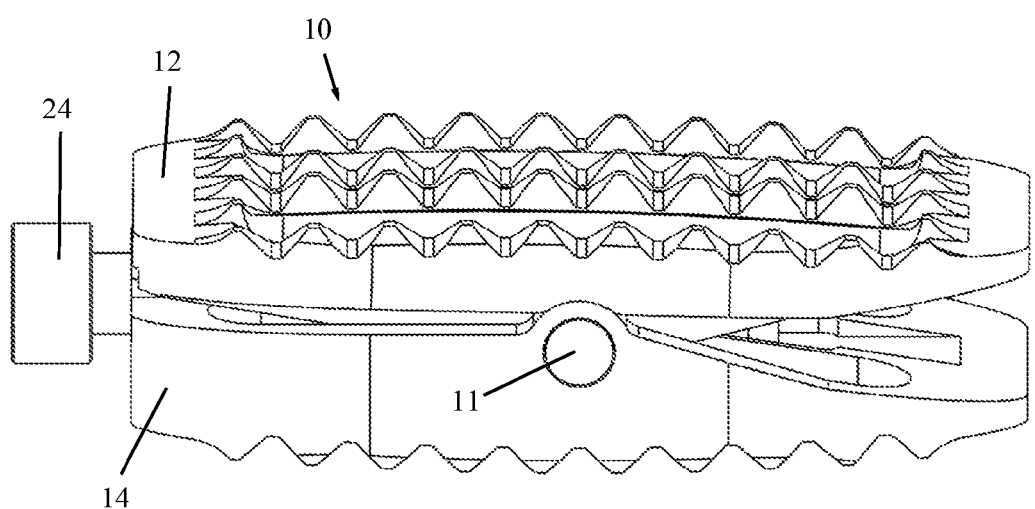

An actuator 24 is linked to wedge element 20 for moving wedge element 20 axially between members 12 and 14 to change the tilt between members 12 and 14. Actuator 22 includes a threaded member 24 (such as a screw) attached to wedge element 20, and a biasing device 26 (such as a spring) positioned between the first or second spinal attachment members 12 and 14 and the wedge element 20. By appropriate turning of threaded member 24, the wedge element 20 is advanced with respect to articulation joint 11 so that first and second spinal attachment members 12 and 14 are tilted (FIGS. 2 and 4) or parallel to each other (FIGS. 3 and 5).

In one mode of operation, the surgeon installs spinal cage 10, such as by means of a lateral access in the patient, and adjusts the threaded member 24 to place wedge element 20 at an initial configuration of first and second spinal attachment members 12 and 14 (e.g., a desired tilted configuration) to help correct curvature of the spine of the patient. After the operation, if the patient succeeds at some point to make a movement that tends to further correct the curvature of the spine (such as by means of post-operational lateral bending exercises and the like), the biasing device 26 will immediately apply a biasing force on wedge element 20 to further move wedge element 20 axially to a new position that maintains the current position of the spine at the newly corrected position. The wedge element 20 remains in the new position by being geometrically locked in the place to which it was pushed by the biasing device 26. In this manner, over time and with gradual further corrective movements of the patient, the system gradually further corrects curvature of the spine.

Contrary to the prior art, in the present invention, both threaded member 24 and biasing device 26 are on the same side of the articulation joint 11. In addition, contrary to the prior art, in the present invention, the wedge element 20 (particularly the chamfered surface 20B) may be coated to reduce friction between the wedge element 20 and the inner surfaces of the first or second spinal attachment members 12 and 14.

What is claimed is:

1. A spinal cage comprising:
   first and second spinal attachment members attachable to vertebrae, said first and second spinal attachment members articulating with one another by means of an articulation joint;
   a wedge element arranged for wedging between said first and second spinal attachment members;
   an actuator linked to said wedge element for moving said wedge element axially with respect to said first and second spinal attachment members, said actuator comprising a threaded member adjacent said wedge element, and wherein upon turning and advancement of said threaded member, said wedge element is advanced with respect to said articulation joint so that said first and second spinal attachment members are tilted or parallel with respect to each other, and wherein said articulation joint does not move linearly with respect to said first and second spinal attachment members; and
   a biasing device arranged to apply a biasing force on said wedge element to advance said wedge element axially in a same direction as advancement of said threaded member.

2. The spinal cage according to claim 1, wherein said threaded member and said biasing device are on a same side of said articulation joint.

3. The spinal cage according to claim 1, wherein said wedge element is coated to reduce friction between said wedge element and inner surfaces of said first and second spinal attachment members.

4. The spinal cage according to claim 1, wherein said articulation joint comprises a male member which is pivotally received in a female member.

5. The spinal cage according to claim 1, wherein said articulation joint permits articulation thereabout in one rotational degree of freedom.

6. The spinal cage according to claim 1, wherein each of said first and second spinal attachment members comprises a bone-interface surface attachable to vertebrae and which are configured to promote osseointegration.

7. The spinal cage according to claim 6, wherein said bone-interface surfaces are shaped to match an anatomical shape of a spinal structure to which said first and second spinal attachment members are to be attached.

8. The spinal cage according to claim 1, wherein said wedge element has a generally flat surface that slides over an inner surface of said second spinal attachment member and a chamfered surface that wedges against an inner surface of said first spinal attachment member.

9. The spinal cage according to claim 1, wherein said biasing device is positioned between said first or second spinal attachment member and said wedge element.

10. The spinal cage according to claim 1, wherein geometrical shapes of said first and second spinal attachment members are configured to accommodate a lordosis angle between adjacent vertebrae.

11. A spinal cage comprising:
   first and second spinal attachment members attachable to vertebrae, said first and second spinal attachment members articulating with one another by means of an articulation joint that defines a pivot axis centrally located between opposite ends of one of said spinal attachment members;
   a wedge element arranged for wedging between said first and second spinal attachment members and movable across said pivot axis;
   an actuator linked to said wedge element for moving said wedge element axially with respect to said first and second spinal attachment members, said actuator comprising a threaded member adjacent said wedge element, and wherein upon turning and advancement of said threaded member, said wedge element is advanced with respect to said articulation joint so that said first and second spinal attachment members are tilted or parallel with respect to each other; and
   a biasing device arranged to apply a biasing force on said wedge element to advance said wedge element axially in a same direction as advancement of said threaded member.

12. A method of using a spinal cage comprising:
   installing a spinal cage in a patient, said spinal cage comprising first and second spinal attachment members attachable to vertebrae, said first and second spinal attachment members articulating with one another by means of an articulation joint; a wedge element arranged for wedging between said first and second spinal attachment members; and an actuator linked to said wedge element for moving said wedge element axially with respect to said first and second spinal attachment members, said actuator comprising a threaded member adjacent said wedge element, and wherein upon turning and advancement of said threaded member, said wedge element is advanced with respect to said articulation joint so that said first and second spinal attachment members are tilted or parallel with respect to each other, and a biasing device arranged to apply a biasing force on said wedge element to move said wedge element axially in a same direction as advancement of said threaded member; and
   adjusting the threaded member to place the wedge element at an initial configuration of said first and second spinal attachment members to help correct curvature of a spine of the patient, wherein the biasing device is configured to apply a biasing force on the wedge element to further advance the wedge element axially from the initial configuration to a new position.

* * * * *